(12) United States Patent
Sundberg et al.

(10) Patent No.: US 6,942,802 B2
(45) Date of Patent: Sep. 13, 2005

(54) REMOVAL OF BACTERIAL ENDOTOXIN IN A PROTEIN SOLUTION BY IMMOBILIZED METAL AFFINITY CHROMATOGRAPHY

(75) Inventors: Rhonda Lunt Sundberg, Siler City, NC (US); Robert Leonard Hopfer, Sanford, NC (US)

(73) Assignee: Wyeth Holdings Corporation, Madison, NJ (US)

( * ) Notice: Subject to any disclaimer, the term of this patent is extended or adjusted under 35 U.S.C. 154(b) by 76 days.

(21) Appl. No.: 10/474,533

(22) PCT Filed: Apr. 5, 2002

(86) PCT No.: PCT/US02/10937

§ 371 (c)(1),
(2), (4) Date: Oct. 10, 2003

(87) PCT Pub. No.: WO02/083710

PCT Pub. Date: Oct. 24, 2002

(65) Prior Publication Data

US 2004/0112832 A1 Jun. 17, 2004

(51) Int. Cl.⁷ .............................................. B01D 15/08
(52) U.S. Cl. .................... 210/635; 210/656; 210/198.2; 530/413
(58) Field of Search ........................ 424/93.1; 604/5.02; 210/635, 656, 659, 198.2; 530/413, 416, 417

(56) References Cited

U.S. PATENT DOCUMENTS

| | | | |
|---|---|---|---|
| 3,897,309 A | | 7/1975 | Grabner |
| 4,276,050 A | | 6/1981 | Firca et al. |
| 4,381,239 A | | 4/1983 | Chibata et al. |
| 5,990,301 A | * | 11/1999 | Colpan et al. ............. 536/25.4 |
| 6,310,190 B1 | * | 10/2001 | Hansen et al. ............. 536/23.1 |
| 6,365,147 B1 | * | 4/2002 | Luo et al. .................. 424/93.1 |

OTHER PUBLICATIONS

Duff et al., Clinical Research, 30, 565A, 1982.

Issekutz, Journal of Immunological Methods, 61:275–281, 1983.

Morrison et al., Immunochemistry, 13:813–818, 1976.

* cited by examiner

*Primary Examiner*—Ernest G. Therkorn
(74) *Attorney, Agent, or Firm*—Bill T. Brazil

(57) ABSTRACT

The present invention relates to the purification of polypeptides and the removal of endotoxin via immobilized metal affinity chromatography (IMAC). More specifically, the invention relates to methods for removing bacterial endotoxin in a protein solution. In specific embodiments, the invention relates to the elimination of endotoxin from *Moraxella catarrhalis* outer membrane proteins.

21 Claims, No Drawings

REMOVAL OF BACTERIAL ENDOTOXIN IN A PROTEIN SOLUTION BY IMMOBILIZED METAL AFFINITY CHROMATOGRAPHY

REFERENCE TO RELATED APPLICATIONS

This application is a 371 of PCT/US02/10937 filed Apr. 5, 2002.

FIELD OF THE INVENTION

The present invention relates generally to the fields of bacteriology, toxicology and protein purification. In particular, the invention relates to the purification of polypeptides and the removal of endotoxin via immobilized metal affinity chromatography (IMAC). More specifically, the invention relates to methods for removing bacterial endotoxin in a protein solution. In specific embodiments, the invention relates to the elimination of endotoxin from *Moraxella catarrhalis* outer membrane proteins.

BACKGROUND OF THE INVENTION

Despite aggressive management, septic shock arising from Gram-negative bacteria sepsis continues to be a leading cause of death in both surgical and medical patients. Death in such patients usually results from cardiovascular collapse and/or multiple organ system failure. One of the most numerous and dominant agents causing sepsis from Gram-negative bacterial infection is endotoxin, which is present on the surface of Gram-negative bacteria, including *Escherichia coli*.

Bacterial endotoxin is a complex consisting of lipid, carbohydrate and protein. It is characterized by an overall negative charge, heat stability and high molecular weight. Highly purified endotoxin does not contain protein, and is comprised of lipopolysaccharide (LPS) and lipooligosaccharide (LOS). Depyrogenation can generally be achieved by inactivating or removing endotoxin, depending upon the physicochemical nature of the LPS. LPS consists of three distinct chemical regions, lipid A, which is the innermost region, an intermediate core polysaccharide, and an outermost O-specific polysaccharide side chain, which is responsible for an endotoxin's particular immunospecificity.

Bacterial endotoxins present severe pathophysiological reactions when introduced into animals, including high fever, vasodilation, diarrhea and, in extreme cases, fatal shock. (Morrison, 1987). Thus, it is critical to avoid endotoxin contamination in any pharmaceutical product or medical device which comes into contact with body fluids. In addition, high endotoxin levels in sera due to bacterial diseases, such as septicemia, are not easily treated. Antibiotic treatment of the infection only kills the bacteria, leaving the endotoxin from their cell walls free to cause fever.

Endotoxins tend to form micellar structures which have a similar density, size, and charge distribution on the outer surface of the micelles. As a result, endotoxins co-purify with proteins or nucleic acids. Various attempts have been made to eliminate endotoxins present in biological and pharmaceutical compositions (U.S. Pat. No. 5,972,225; U.S. Pat. No. 6,132,610; U.S. Pat. No. 6,194,562; U.S. Pat. No. 5,747,455; U.S. Pat. No. 5,169,535; U.S. Pat. No. 5,101,019; U.S. Pat. No. 4,808,314; U.S. Pat. No. 4,059,512 and U.S. Pat. No. 3,959,128) and it has become increasingly evident, that endotoxins are not readily separated from protein or nucleic acid samples. Further, endotoxins are extremely stable, resist extremes of temperature and pH value and have a broad spectrum of biological activity (e.g., are toxic in humans and other animals, are pyrogenic when present in trace amounts, and can cause hypotensive shock, disseminated intravascular coagulation and death).

Bacterial endotoxins thus impede progress in various areas of biotechnology. Gram-negative bacteria can, shed endotoxins from their cell walls and endotoxins are therefore a potential contaminant of any aqueous solution. For example, during lysis of bacterial cells, such as is done in recombinant protein purification or to release plasmids from transformants (e.g., *E. coli*), endotoxins are released into the lysate produced thereby. Endotoxin contamination in protein or nucleic acid samples can adversely limit the utility of the sample, particularly in applications which are sensitive to such contamination (e.g., pharmaceutical compositions). For example, the transfection efficiencies of several different cultured eukaryotic cell lines, including HeLa, Huh7, COS7, and LMH, have been shown to be sharply reduced in the presence of endotoxins (Weber et al., 1995). Endotoxins have also been found to be toxic to primary human cells, such as primary human skin fibroblasts and primary human melanoma cells, in the presence of entry-competent adenovirus particles (Cotton et al., 1994).

Although glassware, plasticware, water, and most buffers can be effectively decontaminated from free endotoxins (see for example, Sofer, 1984; Issekutz, 1983), many proteinaceous macromolecules such as hormones, immunoglobulins, and enzymes are biologically inactive following such treatments. This is a particularly important problem with the recent advances in biotechnology. Bacterial contamination of useful biological products is recognized as a problem (Wightsmith et al., 1982). Endotoxin-producing bacteria used in genetic engineering experiments can add greatly to the risk of endotoxin contamination of materials produced by such techniques.

Ultrafiltration, dialysis and certain chromatographic methods have been employed to remove endotoxin from aqueous solutions. These methods typically separate small molecules from endotoxins based on the size difference between the small molecule and endotoxin, which aggregates into high molecular weight micelles in aqueous solutions. However, endotoxins and many macromolecules are often too similar in size to be separated using these techniques. Additional chromatographic purification techniques, such as adsorbing matrices, affinity chromatography and ion exchange chromatography, have been described to remove endotoxin in a solution (U.S. Pat. No. 3,897,309; U.S. Pat. No. 4,276,050; U.S. Pat. No. 4,381,239; Morrison et al., 1976; Duff et al., 1982; Issekutz, 1983). However, these procedures typically still permit about 10% of the originally present endotoxin to remain in solution or associated with protein following elution from the column (e.g., see Duff et al., 1982). The presence of that 10% protein-associated endotoxin may not affect the endotoxin assay, but still could remain pyrogenic.

*Moraxella catarrhalis* is an important human respiratory tract pathogen. *M. catarrhalis* is the third most common cause of otitis media in infants and children (Murphy, 1989). *Moraxella catarrhalis* is a common cause of sinusitis and conjunctivitis in both children and adults (see e.g., Bluestone, 1986; Brorson et al., 1976; Romberger et al., 1987) and is an important cause of lower respiratory tract infections in adults with chronic bronchitis and chronic obstructive pulmonary disease (Murphy et al., 1992; Catlin, 1990). Additionally, *M. catarrhalis* can cause pneumonia; endocarditis, septicemia, and meningitis in immunocompromised hosts (Cocchi et al., 1968; Douer et al., 1977; McNeely et al., 1976).

Since recurrent otitis media is associated with substantial morbidity, and the attendant health care costs, there is interest in developing strategies for identifying and preventing these infections. One such approach is the development of immunogenic compositions for preventing bacterial otitis media. Outer membrane proteins are being investigated as antigens having utility in diagnosing and immunizing against disease caused by bacterial pathogens, such as *M. catarrhalis*. However, it is imperative in the formulation of these compositions, that the outer membrane protein antigen (s) is effectively free of bacterial endotoxin, so as to prevent sepsis.

Thus, there is presently a need for simple and efficient methods or processes to purify protein samples, effectively free of bacterial endotoxin. It is additionally desirable that such a protein purification method occurs without significant loss in protein concentration or biological activity, such that the protein can be administered (e.g., parenterally) as a pharmaceutical or immunogenic composition, effectively free of endotoxin.

SUMMARY OF THE INVENTION

The present invention relates to the purification of polypeptides and the removal of endotoxin by immobilized metal affinity chromatography (IMAC). More specifically, the invention relates to methods for removing bacterial endotoxin in a protein solution, and in specific embodiments, the elimination of endotoxin from *Moraxella catarrhalis* outer membrane proteins.

Thus, in particular embodiments the present invention is directed to a method for removing bacterial endotoxin in a protein solution using immobilized metal ion affinity chromatography (IMAC) comprising the steps of (a) applying the solution to an IMAC resin, wherein the resin is equilibrated in a buffer; (b) eluting the endotoxin with the buffer of step (a), wherein the protein remains bound to the resin; (c) eluting the protein in an elution buffer comprising glycine; and (d) collecting the eluted protein, wherein the concentration of the endotoxin in the protein solution is effectively reduced by a factor of at least 200 and protein recovery is greater than at least 60%. In preferred embodiments, the concentration of the endotoxin in the protein solution is effectively reduced by a factor of at least 300, more preferably a factor of at least 500, even more preferably a factor of at least 1000 and most preferably a factor of at least 2,500 and protein recovery is greater than at least 65%, more preferably greater than at least 70%, even more preferably greater than at least 80%, yet more preferably greater than at least 85%, and most preferably greater than at least 90 to about 99.9%.

In particularly preferred embodiments, the endotoxin is a lipooligosaccharide (LOS) or a lipopolysaccharide (LPS) and the protein is a Gram negative bacteria protein. In a preferred embodiment, the Gram negative bacteria protein is a *Moraxella catarrhalis* outer membrane protein, more preferably, a *Moraxella catarrhalis* UspA2 protein. In other embodiments of the invention, the buffer of step (a) is selected from the group consisting of sodium phosphate, sodium acetate, 1,4-piperazinebis-(ethanesulfonic acid) (PIPES), N-(2-acetamido)imino-diacetic acid (ADA) and N-(2acetamido)-2-aminoethanesulfonic acid (ACES) and the elution buffer comprising glycine of step (c) is selected from the group consisting of sodium phosphate, sodium acetate, imidazole, histidine, ammonium chloride, PIPES, ADA and ACES. In particular embodiments, the elution buffer of step (c) has a glycine concentration from about 1 mM to about 500 mM. In a preferred embodiment, the buffer of step (a) is sodium phosphate at a concentration of at least about 1 mM to about 50 mM and has a pH of about 6.5 to about 7.8, the buffer further comprising about 150 mM NaCl and 0.1% Triton-X. In a particularly preferred embodiment, the sodium phosphate has a concentration of about 10 mM and a pH of 6.8.

In another preferred embodiment, the elution buffer of step (c) is sodium phosphate at a concentration of at least about 1 mM to about 50 mM and has a pH of about 6.5 to about 7.5, the buffer further comprising about 150 mM NaCl, 0.04% Triton-X and 100 mM glycine. In a particularly preferred embodiment, the sodium phosphate has a concentration of about 10 mM and a pH of 6.8.

In yet other embodiments of the invention, the IMAC resin is charged with a divalent or trivalent cation such as $Cu^{2+}$, $Ni^{2+}$, $Fe^{3+}$, $Co^{2+}$, $Cd^{2+}$, $Ti^{2+}$, $Mg^{2+}$, $Fe^{2+}$, $Mn^{2+}$ or $Zn^{2+}$. In preferred embodiments, the resin is charged with $Cu^{2+}$, $Ni^{2+}$, $Zn^{2+}$ or $Fe^{3+}$, more preferably $Cu^{2+}$. In a most preferred embodiment, the resin is charged with 20 mM cupric sulfate.

In another embodiment, the buffer of step (a) and the elution buffer of step (c) further comprise a mobile phase modifier selected from the group consisting of urea, ethanol, methanol, isopropanol, ethylene glycol and a detergent.

In certain embodiments, the resin is washed prior to step (a) with at least 3 to 10 resin volumes of the buffer used in step (c) and then washed with 1 to 10 resin volumes of the buffer of step (a) wherein the washes remove excess copper from the resin. In another embodiment, the protein solution is diluted in a buffer comprising 10 mM sodium phosphate, 150 mM NaCl and 0.25% Triton-X at pH 6.9, before proceeding to step (a). In additional embodiments, the protein is further purified by ultrafiltration or filtration.

In a particularly preferred embodiment of the invention, an isolated and purified UspA2 protein of *Moraxella catarrhalis* is provided, comprising less than about 0.1 endotoxin units per ug of UspA2 protein. The UspA2 protein is purified by IMAC, the method comprising the steps of (a) applying a Usp2A protein solution to an IMAC resin, wherein the resin is equilibrated in a buffer; (b) eluting the endotoxin with the buffer of step (a), wherein the protein remains bound to the resin; (c) eluting the protein in an elution buffer; and (d) collecting the eluted protein.

Other features and advantages of the invention will be apparent from the following detailed description, from the preferred embodiments thereof, and from the claims.

DETAILED DESCRIPTION OF THE INVENTION

The present invention addresses the need for methods for treating solutions of proteins containing endotoxins to effectively reduce the concentration of endotoxins contained therein. The invention described herein offers a rapid and efficient means for removing endotoxins from such solutions, thereby providing purified proteins which can be used in a variety of biological applications, including but not limited to, in vivo administration of the purified proteins as immunogenic or pharmaceutical compositions.

Thus, in particular embodiments, the invention is directed to the purification of polypeptides and the removal of endotoxin by immobilized metal affinity chromatography (IMAC). More specifically, the invention relates to methods for removing bacterial endotoxin in a protein solution, particularly, endotoxin from *Moraxella catarrhalis* outer membrane proteins by IMAC.

A. Endotoxin Removal and Protein Purification

The present invention is thus directed in particular embodiments, to the removal of bacterial endotoxin. In a preferred embodiment, the invention is directed to a method for removing bacterial endotoxin in a protein solution using immobilized metal ion affinity chromatography (IMAC); the method comprising the steps of applying the solution to an IMAC resin, eluting the endotoxin from the IMAC resin, wherein the protein remains bound to the resin, eluting the protein in an elution buffer comprising glycine and collecting the eluted protein, wherein the concentration of the endotoxin in the protein solution is effectively reduced by a factor of at least 200 and protein recovery is greater than at least 60%.

The use of the phrase "effectively reduced by a factor of at least 200," refers to the endotoxin concentration as determined before and after IMAC purification. Similarly, protein recovery according to the present invention, is the protein concentration as determined before and after IMAC purification. In a preferred embodiment, the concentration of the endotoxin in the protein solution is effectively reduced by a factor of at least 250, more preferably reduced by a factor of at least 500, even more preferably reduced by a factor of at least 1000 fold and most preferably reduced by a factor of at least 2000 fold. In another preferred embodiment, protein recovery is greater than at least 65%, more preferably protein recovery is greater than at least 70%, more preferably yet protein recovery is greater than at least 80%, and most preferably protein recovery is greater than about 95%. In a preferred embodiment, the invention is directed to an isolated and purified UspA2 protein of *Moraxella catarrhalis* comprising less than about 0.1 endotoxin units per ug of UspA2 protein, wherein the protein is purified by the above method.

As mentioned supra, the present invention relates to a method for removing bacterial endotoxin in a protein solution using immobilized metal ion affinity chromatography (IMAC). The principles of IMAC are generally appreciated by those of skill in the art. It is believed that adsorption is predicated on the formation of a metal coordination complex between a metal ion, immobilized by chelation on the adsorbent matrix, and accessible electron donor amino acids on the surface of the protein to be bound. The metal ion microenvironment including, but not limited to, the matrix, the spacer arm, if any, the chelating ligand, the metal ion, the properties of the surrounding liquid medium and the dissolved solute species can be manipulated by the skilled artisan to effect the desired fractionation.

Not wishing to be bound by any particular theory as to mechanism, it is further believed that the more important amino acid residues in terms of binding are histidine, tryptophan and probably cysteine. Since one or more of these residues are generally found in proteins, one might expect all proteins to bind to IMAC resins. However, the residues not only need to be present but also accessible (e.g., oriented on the surface of the protein) for effective binding to occur to the resin. Thus, the present invention also contemplates the addition of appropriate residues to a protein of interest. For example, poly-histidine tails added to the amino terminus or carboxy terminus of a protein, can be engineered into a recombinant expression system (as described in U.S. Pat. No. 4,569,794) to either permit or enhance resin binding. Thus, it is contemplated here, that the addition of appropriate residues might be employed in order to facilitate endotoxin removal from a protein solution, wherein the protein does not bind or binds weakly to the IMAC resin in the absence of such residue additions.

The nature of the metal and the way it is coordinated on the resin can also influence the strength and selectivity of the binding reaction. Matricies of silica gel, agarose and synthetic organic molecules such as polyvinyl-methacrylate co-polymers can be employed. The matricies preferably contain substituents to promote chelation. Substituents such as iminodiacetic acid (IDA) or its tris (carboxymethyl) ethylene diamine (TED) can, be used, wherein IDA is preferred. A particularly useful IMAC material is a polyvinyl methacrylate co-polymer substituted with IDA available commercially, e.g., as TOYOPEARL AF-CHELATE 650M (ToyoSoda Co.; Tokyo). Another useful IMAC ligand is nitrilotriacetic acid, comprising four available metal binding sites. The metals are preferably divalent cations (e.g., $Zn^{2+}$, $Cu^{2+}$, $Ni^{2+}$, $Co^{2+}$, $Fe^{2+}$, $Mn^{2+}$, $Ti^{2+}$, $Cd^{2+}$ and $Mg^{2+}$), with $Cu^{2+}$ being the most preferred, but may also be trivalent cations such as $Fe^{3+}$. An important selection parameter is of course, the affinity of the protein to be purified for a particular metal.

In practice the IMAC column is "charged" with a metal by pulsing with a concentrated metal salt solution followed by water or buffer. A pre-wash with intended elution buffers is usually carried out. Sample buffers may contain salt up to 1M or greater to minimize nonspecific ion-exchange effects. Adsorption of proteins is maximal at higher pHs. Elution is normally either by lowering of pH to protonate the donor groups on the adsorbed protein, or by the use of stronger complexing agent such as imidazole, or glycine buffers. In these latter cases, the metal may also be displaced from the column. Linear gradient elution procedures can also be beneficially employed.

Although the present invention is directed to the purification of polypeptides and the removal of endotoxin by immobilized metal affinity chromatography (IMAC), additional purification and/or processing of the protein sample obtained by IMAC purification may additionally be carried out using techniques common in the art. For example, the protein may additionally be purified by ion exchange chromatography, affinity chromatography, hydrophobic interaction chromatography, high purity liquid chromatography, fast purity liquid chromatography, ultrafiltration, diafiltration, dialysis, and/or ethanol precipitation. Further, the protein may be additionally concentrated by ultrafiltration, diafiltration, ethanol precipitation and the buffer/salt composition exchanged by dialysis, ultrafiltration, ethanol precipitation and/or ion exchange chromatography.

Conditions such as salt concentrations, buffer composition, ionic strength, pH and the like, are readily determined by the skilled artisan, and are often an empirical determination, dependent on the macromolecules to be separated or purified. For example, binding of endotoxin according to the present invention typically occurs in the pH range of 5.5–8.5. In addition, alternative buffers and concentration ranges for promoting endotoxin-IMAC binding are 0.01–0.2 M sodium phosphate and 0.05 M sodium acetate. NaCl concentrations of 0.15–0.5 M may further be included in the "binding buffer" to prevent ion exchange effects. Commonly used buffers for elution are 0–0.5 M imidazole, 0–0.05 M histidine, 0–2 M ammonium chloride. Chelating agents such as 0.05 M EDTA or EGTA may be used in certain formulations, but will strip the column of the metal. Mobile phase modifiers such as urea, isopropanol (other alcohols), ethylene glycol or detergents may also be used to elute or improve separation (see, Franken et al., 2000).

The surface of Gram-negative bacteria comprises endotoxin, which can be shed endotoxins from their cell walls. Bacterial endotoxin is a complex consisting of lipid, carbohydrate and protein. It is characterized by an overall negative charge, heat stability and high molecular weight. Highly purified endotoxin does not contain protein, and is a lipopolysaccharide (LPS). Depyrogenation can generally be achieved by inactivating or removing endotoxin, depending upon the physicochemical nature of the LPS. LPS consists of three distinct chemical regions, lipid A, which is the innermost region, an intermediate core polysaccharide, and an outermost O-specific polysaccharide side chain, which is responsible for an endotoxin's particular immunospecificity. Endotoxins tend to form micellar structures which have a similar density, size, and charge distribution on the outer surface of the micelles. Some proteins, particularly lipoproteins and monoclonal antibodies, are known to disaggregate endotoxins and form complexes with LOS or LPS in solution, which increases the difficulty for separating the endotoxin and protein (Liping et al., 1997). Bacterial endotoxin is typically quantitated using the LAL Kinetic-Turbidimetric Method (Toxinometer Assay). In this method, the endotoxin concentration is measured by optically monitoring the increasing turbidity of a sample, resulting from an endotoxin-dependent gelation of the limulus amebocyte lysate (LAL).

B. Recombinantly Expressed *Moraxella catarrhalis* UspA2 Polypeptides

In certain embodiments of the invention, an isolated and purified UspA outer membrane protein of *Moraxella catarrhalis* is provided, comprising less than about 0.1 endotoxin units per ug of UspA2 protein. The UspA2 protein is purified by IMAC, the method comprising the steps of (a) applying a UspA2 protein solution to an IMAC resin, wherein the resin is equilibrated in a buffer; (b) eluting the endotoxin with the buffer of step (a), wherein the protein remains bound to the resin; (c) eluting the protein in an elution buffer comprising glycine; and (d) collecting the eluted protein.

Thus, in particular embodiments, the invention contemplates the purification of *Moraxella catarrhalis* UspA2 protein. Preferably, a UspA2 protein of the invention is a recombinant protein. Typically, a UspA2 protein is produced by recombinant expression in a non-human cell, preferably a prokaryotic cell, and most preferably a Gram-negative cell, in particular, an *E. coli* cell. In certain embodiments, a UspA2 protein is a full length UspA2 protein, whereas in other embodiments it may be a UspA2 protein fragment. Expression vectors would thus comprise a UspA2 polynucleotide or fragment thereof that encodes a UspA2 polypeptide or its fragment. Expression of proteins in prokaryotes is most often carried out in *E. coli* with vectors containing constitutive or inducible promoters directing the expression of either fusion or non-fusion proteins. Fusion vectors add a number of amino acids to a protein encoded therein, to the amino or carboxy terminus of the recombinant protein.

Examples of inducible *E. coli* expression vectors include pTrc (Amann et al., 1988) and pET I I d (Studier et al., 1990). Vector DNA can be introduced into prokaryotic or eukaryotic cells via conventional transformation, infection or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. ("Molecular Cloning: A Laboratory Manual" 2nd. Ed. Cold Spring Harbor Laboratory, Cold Spring Harbor Laboratory Press, Cold Spring Harbor, N.Y., 1989), and other laboratory manuals.

A host cell of the invention, such as a prokaryotic host cell in culture, can be used to produce (i.e., express) UspA2 polypeptides. Accordingly, the invention further provides methods for producing UspA2 polypeptides using the host cells of the invention. The method comprises culturing the host cell (into which a recombinant expression vector encoding a UspA2 polypeptide has been introduced) in a suitable medium until the UspA2 polypeptide is produced. The method further comprises isolating the UspA2 polypeptide from the medium or the host cell.

In another aspect, the recombinant host cells of the present invention are prokaryotic host cells. Preferably, the recombinant host cells of the invention are bacterial cells of the DH5 α strain of *Escherichia coli*. In general, prokaryotes are preferred for the initial cloning of DNA sequences and constructing the vectors useful in the invention. For example, *E. coli* K12 strains can be particularly useful. Other microbial strains which can be used include *E. coli* B, and *E. coli$_x$*1976 (ATCC No. 31537).

Other prokaryotic strains, such as *E. coli* W3110 (ATCC No. 273325), bacilli such as *Bacillus subtilis*, or other enterobacteriaceae such as *Salmonella typhimurium* or *Serratia marcesans*, and various *Pseudomonas* species can also be used for expression. These examples are, of course, intended to be illustrative rather than limiting.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* can be transformed using pBR322, a plasmid derived from an *E. coli* species (Bolivar, et al. 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (Chang, et al. 1978; Itakura, et al. 1977, Goeddel, et al. 1979; Goeddel, et al 1980) and a tryptophan (TRP) promoter system (International Application No. EP 0036776; Siebwenlist et al. 1980). While these are the most commonly used, other microbial promoters have been discovered and utilized, and details concerning their nucleotide sequences have been published, enabling a skilled worker to introduce functional promoters into plasmid vectors (Siebwenlist, et al. 1980).

EXAMPLES

The following examples are carried out using standard techniques, which are well known and routine to those of skill in the art, except where otherwise described in detail. The following examples are presented for illustrative purpose, and should not be construed in any way limiting the scope of this invention.

Example 1

Analytical Methods

SDS-PAGE and LOS Western Blot Analysis

SDS-PAGE samples were prepared by mixing 1:1 with 2× sample buffer and heating at 100° C. for 10 minutes.

Samples were loaded onto 4–12% (wt./vol.) Tris-glycine polyacrylamide gels (Zaxis) and stained with Coommassie blue (Zoion). LOS Western Blot analysis was performed using 4–20% (wt./vol.) polyacrylamide gels that were transferred by electrophoresis onto nitrocellulose membranes (BioRad). The nitrocellulose was blocked in Tris buffered saline (TBS) containing 3% (wt./vol.) BSA for 1 hour and then washed 3 times with Tris buffered saline containing 0.05% Tween 20 (TTBS). The membranes were placed in a primary antibody solution containing a monoclonal antibody specific for lipooligosaccharide purified from *Moraxella catarrhalis* (MAb 73-11, lot#121294) diluted in TBS containing 1% BSA and incubated at room temperature for 1 hour. The membranes were washed 3 times with TTBS followed by incubation in the secondary antibody solution of Goat anti-mouse IgG-HRP (BioRad) diluted in TBS containing 1% BSA for 1 hour at room temperature. After incubation in the secondary antibody solution, the membranes were washed 3 times with TTBS and then 3 times with TBS. The blots were developed using a substrate containing 4-chloro-1-naphthol at a concentration of 1.4 g/l in an organic base mixed 1:1 with a solution composed of 0.02% $H_2O_2$ in a Citric Acid buffer (KPL, Gaithersburg, Md.) *Moraxella cattarrahlis* lipooligosaccharide (LOS) used as a standard was prepared from strain ATCC25238 by the modified Westphal method (Westphal and Jann, 1965).

Total Protein, Limulus Amebocyte Lysate (LAL) Assay and Residual Copper Analysis Total protein was determined by the microbicinchoninic acid assay (Pierce, Rockford, Ill.). LAL Analysis was performed according to the Guideline on Validation of the Limulus Amebocyte Lysate test as an End-product Endotoxin Test for Human and Animal Parenteral Drugs, Biological Products, and Medical Devices, December 1987, U.S. Department of Health and Human services, FDA and Interim Guidance for same, July 1991. Residual copper analysis was performed by graphite Furnace atomic Absorption Spectroscopy.

Example 2

Screening of UspA2 and LOS for Affinity to Chelated Metal Ions

UspA2 is an outer membrane protein purified from *Moraxella catarrhalis*, a Gram negative bacteria. The protein has a molecular mass of 62 kDa, but exists as an oligomer and runs at approximately 240 kDa by SDS-PAGE analysis.

UspA2 and LOS were screened for affinity to chelated metal ions bound to IDA resin. Two milliliters of Pharmacia chelating sepharose fast flow resin was placed in a test tube. The resin was washed twice with 4 mL of water for injection (WFI), allowed to settle between washes and the supernatant removed. The resin was then charged with 4 mL of one of the following metal ion solutions: 5 mg/mL $CuSO_4$, 5 mg/mL $NiSO_4$, 5 mg/mL $ZnCL_2$ or 0.1 M $FeCl_3$. After the resin settled, the supernatant was removed. This was followed by 5 washes of 4 mL WFI allowing the resin to settle between washes and removal of the supernatant. The resin was then washed with 5–10 volumes of equilibration buffer (10 mM sodium phosphate/0.5 M NaCl/0.1% Triton X-100/ pH 7.2). A 2 mL solution containing 0.1 mg/mL of purified UspA2 in equilibration buffer was added to the resin. The resin was incubated in the solution for 15 minutes with gentle shaking at room temperature. Then the resin was allowed to settle and the supernatant was removed. The resin was washed with three volumes of equilibration buffer, allowing the resin to settle and removing the supernatant between washes. Four milliliters of elution buffer (10 mM sodium phosphate/0.5 M NaCl/100 mM glycine/0.1% Triton X-100/pH 7.0) was added to the resin and incubated with gentle shaking at room temperature. After incubation, the resin was allowed to settle and the supernatant removed. The resin was again treated with 4 mL of elution buffer and incubated with gentle shaking at room temperature. After the second incubation, the resin was again allowed to settle and the supernatant removed. The samples were pooled and analyzed by SDS-PAGE and LOS Western Blot.

SDS-PAGE analysis revealed that all of the UspA2 bound after loading onto the $Cu^{2+}$ charged resin and could not be detected in the supernatant The protein bound less well to the $Ni^{2+}$ charged resin with some residual protein detected in the supernatant after loading. UspA2 binding to the $Zn^{2+}$ and $Fe^{3+}$ charged resins was not detected. LOS Western Blot analysis indicated that the contaminating LOS in the UspA2 protein solution did not bind to any of the metal ions tested. Virtually all of the LOS detected by LOS Western Blot analysis was in the supernatant after the resin was loaded. Some residual LOS was detected in the supernatant after elution of the protein, which is most likely due to residual LOS that was not removed in the supernatant after loading. Based on the affinity of UspA2 for $C^{2+}$, the inventors proceeded to run a small scale $Cu^{2+}$ charged IMAC column that would allow the purification of enough protein to test the final product for LAL.

Example 3

Small Scale Chromatography

A 157 mL (5 cm×8 cm) column was packed using Pharmacia Chelating Sepharose Fast flow resin according to the manufacturer instructions. The column was washed with 8 column volumes (CV) of water for Injection (WFI) and then charged using 3 CV of copper charging solution (5 mg/mL $CuSO_4$) using the flow rates recommended by the manufacturer. Followed by washing with equilibration buffer (10 mM sodium phosphate/0.5 M NaCl/0.1% Triton X-100, pH 7.0) for 15 CV. The column was then pre-washed with 25 CV of elution buffer (10 mM sodium phosphate/0.5 M NaCl/100 mM glycine/0.1% Triton X-100, pH 7.0) followed by 14 CV of equilibration buffer (10 mM sodium phosphate/0.5 M NaCl/0.1% Triton X-100, pH 7.0) to remove any residual copper not tightly bound to the resin. The column was then loaded with 15 mg UspA2 diluted to 0.1 mg/mL in equilibration buffer (10 mM sodium phosphate/0.5 M NaCl/0.1% Triton X-100, pH 7.0). After loading, the column was washed again with 3 CV of equilibration buffer (10 mM sodium phosphate/0.5 M NaCl/ 0.1% Triton X-100, pH 7.0). UspA2 was eluted in 10 mM sodium phosphate/0.5 M NaCl/0.1% Triton X-100, pH 7.0 for 10 CV over a linear gradient from 0–100 mM glycine in order to determine the optimal concentration of glycine for elution of the protein. SDS-PAGE and LOS Western Blot analysis were performed on samples of the flow through during loading, washes after loading and fractions taken during elution of the protein. Those fractions containing UspA2 were pooled. The UspA2 fraction pool was concentrated and diafiltered 5 fold over a 50 $cm^2$ 100K molecular weight cut-off (MWCO) regenerated cellulose Millipore membrane against 10 mM sodium phosphate/100 mM glycine/0.025% Triton X-100, pH 7.0 to reduce residual copper. This was followed by 5 fold diafiltration against PBS containing 0.025% Triton X-100 (10 mM sodium phosphate/

150 mM NaCl/0.025% Triton X-100, pH 7.0). The final diafiltered retentate was then filtered through a 0.2 um Millipak 20.

The final batch concentrate was analyzed for total protein, SDS-PAGE, LAL and residual copper. The IMAC column reduced the endotoxin from 21.6 EU/ug to <0.1 EU/ug based on LAL analysis (Table 1). The protein recovery was 83% based on BCA results after 0.2 um filtration. Residual copper analysis indicated that there was 30 ppb copper remaining after ultrafiltration and 0.2 um filtration. SDS-PAGE analysis indicated that UspA2 bound to the resin, as there was no protein detected in the column flow through during loading or in the washes with equilibration buffer after loading. UspA2 eluted off of the column between 20–50 mM glycine in 10 mM NaPO4/0.5 M NaCL/0.1% Triton X-100. LOS Western Blot analysis showed that the endotoxin (LOS) did not bind to the resin, but came off during loading and within 4 column volumes of washing in equilibration buffer after loading. The amount of endotoxin in the UspA2 containing fractions was less than 1 ng as determined by LOS Western Blot analysis. These fractions were pooled before proceeding to the next purification step in the process, which is ultrafiltration.

TABLE 1

Small Scale Chromatography

| Process Step | SDS-PAGE Estimated Total Protein | Total Protein (BCA) | LAL | Residual Copper (ug/L) |
|---|---|---|---|---|
| UspA2 Loaded onto IMAC Column | 15 mg | 15 mg | 21.6 EU/ug | ND |
| UspA2 IMAC Fraction Pool | 11 mg | 20 mg | ND | 4594 ug/L (4.6 ppm) |
| UspA2 after Ultrafiltration (contained a precipitate) | 11 mg | 17.8 mg | ND | ND |
| UspA2 After Ultrafiltration/ 0.2 um filt. (precipitate was removed by 0.2 um filtration) | 11 mg | 12.5 mg | <0.1 EU/ug | 30 ug/L (30 ppb)# |

The specification for copper in U.S. drinking water is <1.3 ppm.
ND = not detected at the lower limit of detection, which is <0.05 EU/ug for LAL and <2 ppb for copper.

Example 4

Scale up of IMAC Chromatography

An 1113 mL (9 cm×17.5 cm) column was packed using Pharmacia Chelating Sepharose Fast™ flow resin according to the manufacturer instructions. The column was charged using 2 CV of copper charging solution (5 mg/mL $CuSO_4$). Followed by washing with 4 CV of WFI followed by equilibration buffer (10 mM sodium phosphate/0.5 M NaCl/ 0.1% Triton X-100, pH 6.8). The column was then pre-washed with 20 CV of elution buffer (10 mM sodium phosphate/0.5 M NaCl/100 mM glycine/0.1% Triton X-100, pH 7.0) followed by 10 additional column volumes of equilibration buffer (10 mM sodium phosphate/0.5 M NaCl/ 0.1% Triton X-100, pH 6.8) to remove any residual copper not tightly bound to the resin. The column was then loaded with 99 mg UspA2 diluted to 0.1 mg/mL in equilibration buffer (10 mM sodium phosphate/0.5 M NaCL/0.1% Triton X-100, pH 6.8). After loading, the column was washed again with 10 CV of equilibration buffer (10 mM sodium phosphate/0.5 M NaCl/0.1% Triton X-100, pH 6.8). A step gradient was performed in 10 mM sodium phosphate/0.5M NaCl/100 mM glycine/0.1% Triton X-100, pH 6.8 for 15 CV to elute UspA2. SDS-PAGE and LOS Western Blot analysis were performed on samples of the flow through during loading, washes after loading and fractions taken during elution of the protein. Those fractions containing UspA2 were pooled. The UspA2 fraction pool was concentrated and diafiltered 13.5 fold over a 50 $cm^2$ 100K regenerated cellulose Millipore membrane against PBS (10 mM sodium phosphate/150 mM NaCl, pH 7.0). The final diafiltered retentate was then filtered through a 0.2 um Millipak 20. The final batch concentrate was analyzed for total protein, SDS-PAGE, LAL, pyrogenicity and residual copper.

SDS-PAGE analysis of column flow through indicated that UspA2 bound to the resin as in Example 2 and there was no protein detected in the column load or column washes in equilibration buffer after loading. UspA2 eluted after 1.5 column volumes of elution buffer and LOS Western Blot analysis indicated that the endotoxin (LOS) did not bind to the resin but came off during loading and within 6 column volumes of washing in equilibration buffer after loading. LOS Western Blot analysis indicated that there was <1 ng LOS present in the fractions containing UspA2. These fractions were pooled (fractions 6 through 16) and concentrated on a 100K regenerated cellulose filter. After concentration by ultrafiltration, protein recovery was 76% by BCA analysis (Table 2). Twenty milligrams of the concentrated retentate was then diafiltered against 10 mM NaPO4/150 mM NaCl pH 7.2. Triton X-100 was not added to the diafiltration buffer in order to minimize build-up of the detergent on the ultrafiltration membrane. Recovery after diafiltration was 100%, based on BCA analysis. There was no precipitation observed during concentration or diafiltration. Endotoxin was reduced from 21.6 EU/ug to <0.1 EU/ug. Residual copper analysis after ultrafiltration was 80 ppb.

TABLE 2

Scaled-up Chromatography

| Process Step | SDS-PAGE Estimated Total Protein | Total Protein BCA | LAL | Residual Copper |
|---|---|---|---|---|
| UspA2 Loaded onto IMAC Column | 99 mg | 99 mg | 21.6 EU/ug | ND |
| UspA2 IMAC Fraction Pool | 90 mg | 98 mg | ND | 11 ppm |
| UspA2 after Concentration before Diafiltration | 90 mg | 75.8 mg | ND | 6.4 ppm |
| UspA2 After Ultrafiltration/ 0.2 um filt. | 19 mg | 20 mg* | <0.1 EU/ug | 39 ppb# |
| UspA2 After Ultrafiltration/ 0.2 um filt. | 60 mg | 53 mg* | <0.1 EU/ug | 80 ppb# |

*20 mg of the concentrated retentate was initially processed by diafiltration against 10 mM sodium phosphate/150 mM NaCl pH7.2. The remainder (53 mg) was diafiltered as a separate aliquot to minimize loss in the event of diafiltration failure.
The specification for copper in U.S. drinking water is <1.3 ppm.
ND = not detected at the lower limit of detection, which is <0.05 EU/ug for LAL and <2 ppb for copper.

Example 5

Chromatography Method Used for Determination of Resin Capacity for UspA2

A 10 mL (1.6 cm×5 cm) column was packed with Pharmacia Chelating Sepharose Fast flow resin according to the manufacturer's instructions. The column was washed with a minimum of 8 CV of WFI, followed by a minimum of 3 CV of copper charging solution (5 mg/mL CuSO$_4$). The column was then washed with additional WFI followed by >10 CV of elution buffer (10 mM sodium phosphate/0.5 M NaCL/ 100 mM glycine/0.1% Triton X-100, pH 7.0). After equilibrating the column with a minimum of 10 CV equilibration buffer (10 mM sodium phosphate/0.5 M NaCl/0.1% Triton X-100, pH 7.0), the column was loaded with different protein concentrations per milliliter of resin ranging from 1 mg/mL, 0.5 mg/mL, 0.3 mg/mL. The protein was washed onto the column with a minimum of 10 CV of equilibration buffer (10 mM sodium phosphate/0.5 M NaCl/0.1% Triton X-100, pH 7.0). Then eluted with a minimum of 10 CV elution buffer (10 mM sodium phosphate/0.5 M NaCL/100 mM glycine/0.1% Triton X-100, pH 7.0. SDS-PAGE was performed on samples of the flow through during loading, washes after loading and fractions taken during elution of the protein.

SDS-Page analysis indicated that loading of the column at 1 mgUspA2/mL of resin and at 0.5 mg UspA2/mL of resin resulted in the flow through of the protein in the column during loading and the post-load wash with equilibration buffer (data not shown). This was not observed when the column was loaded at 0.3 mg UspA2/mL resin. This suggests that using the buffer conditions described in Example 4, the binding capacity of the resin for this protein is approximately 0.3–0.5 mg UspA2/mL of resin.

Example 6

Chromatography Method Used for Determining Elution Conditions in Buffer Prepared at 0.04% Triton X-100 Concentration An additional experiment was done in the same manner as described above for determination of resin capacity at 0.3 mg UspA2/mL of resin, except the protein was eluted using an elution buffer containing 0.04% Triton X-100 instead of the elution buffer containing 0.1% Triton X-100. The purpose of this experiment was to determine if the protein and LOS would display the same properties if the Triton X-100 concentration was lowered. SDS-PAGE and LOS Western Blot analysis were performed on samples of the flow through during loading, washes after loading and fractions taken during elution of the protein.

Reducing the Triton X-100 concentration from 0.1% to 0.04% appeared to have no effect on the elution of UspA2 off of the column. LOS Western Blot analysis indicated, as in previous experiments, that when the column was loaded at 0.3 mg UspA2/mL of resin, the endotoxin did not bind to the resin and washed through the column during loading and during the post-load washes with equilibration buffer (data not shown).

REFERENCES

U.S. Pat. No. 3,897,309
U.S. Pat. No. 3,959,128
U.S. Pat. No. 4,059,512
U.S. Pat. No. 4,276,050
U.S. Pat. No. 4,381,239
U.S. Pat. No. 4,808,314
U.S. Pat. No. 5,101,019
U.S. Pat. No. 5,169,535
U.S. Pat. No. 5,747,455
U.S. Pat. No. 5,972,225
U.S. Pat. No. 6,132,610
U.S. Pat. No. 6,194,562
U.S. Pat. No. 4,569,794.
Bluestone, *Drugs* 31:S132–S141, 1986.
Brorson et al., *Scand. J. Infect. Dis.* 8:151–155, 1976.
Catlin, *Clin. Microbiol. Rev.* 3:293–320, 1990.
Cocchi et al., *Acta Paediatr. Scand.* 57:451–3, 1968.
Cotton et al., *Gene Therapy* 1:239–246, 1994.
Douer et al., *Ann. Intern. Med.* 86:116–119, 1977. *Duff et al., Clinical Research*, 30, 565A, 1982.
Franken, et al., "Purification of his-tagged proteins by immobilized chelate affinity chromatography: the benefits from the use of organic solvent," *Protein Expr Purif.* 18 (1):95–99, 2000.
Issekutz, *J. Immunol. Methods,* 61: 275–281, 1983.
Liping et al., "Protein Concentration Effect on Protein-Lipopolysaccharide (LPS) Binding and Endotoxin Removal," *Biotechnology Letters*, Vol. 19:135–138, 1997.
McNeely et al., *Am. Rev. Respir. Dis.* 114:399–402, 1976.
Morrison et al., Immunochemistry, 13:813–818, 1976.
Morrison et al., *Immunochemistry,* 13:813–818, 1976.
Morrison, *Ann Rev. Med.* 38:417–32, 1987.
Murphy et al., *Am. Rev. Respir. Dis.* 146:1067–1083, 1992.
Murphy, *Pediatr. Infect: Dis. J.* 8:S75–S77, 1989.
Romberger et al., *South. Med. J.* 80:926–928, 1987.
Sofer, *Biotechnology,* 2:1035–1038, 1984.
Weber et al., *BioTechniques* 19(6):930–939, 1995.
Westphal and Jann, *Methods in Carbohydrate Chemistry* edited by R. L. Whistler, J. N. BeMiller, and M. L. Wolfrom, Vol. 5, p.83, Academic Press, NY, 1965.
Wightsmith et al., *Prog. Clin. Biol. Res.* 43, 287, 1982.

What is claimed is:

1. A method for removing bacterial endotoxin in a protein solution using immobilized metal ion affinity chromatography (IMAC) comprising the steps of:
   (a) applying the solution to an IMAC resin, wherein the resin is equilibrated in a buffer;
   (b) eluting the endotoxin with the buffer of step (a), wherein the protein remains bound to the resin;
   (c) eluting the protein in an elution buffer comprising glycine; and
   (d) collecting the eluted protein,
wherein the concentration of the endotoxin in the protein solution is effectively reduced by a factor of at least 200 and protein recovery is greater than at least 60%.

2. The method of claim 1, wherein the endotoxin is a lipooligosaccharide (LOS) or a lipopolysaccharide (LPS).

3. The method of claim 1, wherein the protein is a Gram negative bacteria protein.

4. The method of claim 3, wherein the protein is a *Moraxella catarrhalis* outer membrane protein.

5. The method of claim 4, wherein the protein is UspA2.

6. The method of claim 1, wherein the glycine of step (c) is at a concentration of at least 1 mM to at least about 500 mM.

7. The method of claim 1, wherein the buffer of step (a) is selected from the group consisting of sodium phosphate, sodium acetate, 1,4-piperazinebis-(ethanesulfonic acid) (PIPES), N-(2-acetamido)imino-diacetic acid (ADA) and N-(2acetamido)-2-aminoethanesulfonic acid (ACES).

8. The method of claim 7, wherein the buffer of step (a) further comprises NaCl at a concentration of at least about 100 mM to about 500 mM.

9. The method of claim 8, wherein the buffer of step (a) is sodium phosphate at a concentration of at least about 1 mM to about 50 mM and has a pH of about 6.5 to about 7.8, the buffer further comprising about 150 mM NaCl and 0.1% Triton-X.

10. The method of claim 9, wherein the sodium phosphate has a concentration of about 10 mM and a pH of 6.8.

11. The method of claim 1, wherein the elution buffer of step (c) is selected from the group consisting of sodium phosphate, sodium acetate, imidazole, histidine, ammonium chloride, PIPES, ADA and ACES.

12. The method of claim 11, wherein the elution buffer of step (c) further comprises NaCl at a concentration of at least about 100 mM to about 500 mM.

13. The method of claim 12, wherein the elution buffer of step (c) is sodium phosphate at a concentration of at least about 1 mM to about 50 mM and has a pH of about 6.5 to about 7.8, the buffer further comprising about 150 mM NaCl, 0.04% Triton-X and 100 mM glycine.

14. The method of claim 13, wherein the sodium phosphate has a concentration of about 10 mM and a pH of 6.8.

15. The method of claim 1, wherein the resin is charged with $Cu^{2+}$, $Ni^{2+}$, $Co^{2+}$, $Fe^{2+}$, $Mn^{2+}$, $Ti^{2+}$, $Cd^{2+}$, $Mg^{2+}$, $Zn^{2+}$ or $Fe^{3+}$.

16. The method of claim 15, wherein the resin is charged with 20 mM cupric sulfate.

17. The method of claim 1, wherein the buffer of step (a) and the elution buffer of step (c) each further comprise a mobile phase modifier selected from the group consisting of urea, isopropanol, ethanol, methanol, ethylene glycol and a detergent.

18. The method of claim 1, wherein the concentration of the endotoxin in the protein solution is effectively reduced by a factor of at least 2,500 and protein recovery is greater than at least 90%.

19. The method of claim 1, wherein the resin is washed prior to step (a) with at least 3 to 10 resin volumes of the buffer used in step (c) and then washed with 1 to 10 resin volumes of the buffer used in step (a), wherein the washes remove excess copper from the resin.

20. The method of claim 1, wherein the protein solution is diluted in a buffer comprising 10 mM sodium phosphate, 150 mM NaCl and 0.25% Triton-X at pH 6.9, before proceeding to step (a).

21. The method of claim 1, wherein the protein is further purified by ultrafiltration or filtration.

* * * * *